(12) United States Patent
Taulu et al.

(10) Patent No.: US 10,307,105 B2
(45) Date of Patent: Jun. 4, 2019

(54) METHOD AND DEVICE FOR RECOGNIZING AND REMOVING UNDESIRED ARTIFACTS IN MULTICHANNEL MAGNETIC FIELD OR ELECTRIC POTENTIAL MEASUREMENTS

(71) Applicant: Elekta AB, Stockholm (SE)

(72) Inventors: Samu Taulu, Helsinki (FI); Matti Kajola, Helsinki (FI); Juha Simola, Helsinki (FI)

(73) Assignee: Elekta AB, Stockholm (SE)

( * ) Notice: Subject to any disclaimer, the term of this patent is extended or adjusted under 35 U.S.C. 154(b) by 812 days.

(21) Appl. No.: 14/374,365

(22) PCT Filed: Jan. 24, 2013

(86) PCT No.: PCT/IB2013/050595
§ 371 (c)(1),
(2) Date: Jul. 24, 2014

(87) PCT Pub. No.: WO2013/111072
PCT Pub. Date: Aug. 1, 2013

(65) Prior Publication Data
US 2014/0343882 A1    Nov. 20, 2014

(30) Foreign Application Priority Data
Jan. 24, 2012 (FI) .................................... 20125075

(51) Int. Cl.
*H04B 1/10*     (2006.01)
*A61B 5/00*     (2006.01)
(Continued)

(52) U.S. Cl.
CPC .............. *A61B 5/7203* (2013.01); *A61B 5/04* (2013.01); *G01R 29/12* (2013.01); *G01R 33/02* (2013.01);
(Continued)

(58) Field of Classification Search
CPC ............................. A61B 5/7203; G01R 33/56
See application file for complete search history.

(56) References Cited

U.S. PATENT DOCUMENTS

2008/0161714 A1    7/2008 Ahonen et al.

FOREIGN PATENT DOCUMENTS

JP    2006520892    9/2009
WO   2003067267    8/2003
(Continued)

OTHER PUBLICATIONS

Giulia Barbatia, Camillo Porcaroa, Filippo Zappasodi, Paolo Maria Rossini, Franca Tecchio; "Optimization of an independent component analysis approach for artifact identification and removal in magnetoencephalographic signals;" 2004; Elsevier; Clinical Neurophysiology; pp. 1220-1232.*

(Continued)

*Primary Examiner* — Mischita L Henson
*Assistant Examiner* — Christine Y Liao
(74) *Attorney, Agent, or Firm* — Michael Best & Friedrich LLP

(57) ABSTRACT

The present invention introduces a method, device and a computer program for removing artifacts present in individual channels of a multichannel measurement device. At first, a basis is generated defining an n-dimensional subspace of the N-dimensional signal space, where n is smaller than N, where using in the definition of the n-dimensional basis a physical model of a Signal Space Separation method, or a statistical model based on the statistics of recorded N-dimensional signals. Thereafter, a combined (n+m)-dimensional basis is formed by adding m signal vectors to the n-dimensional basis, each of these m signal vectors representing a signal present only in a single channel of the N-channel device. After this the recorded N-dimensional (Continued)

Figure 1:
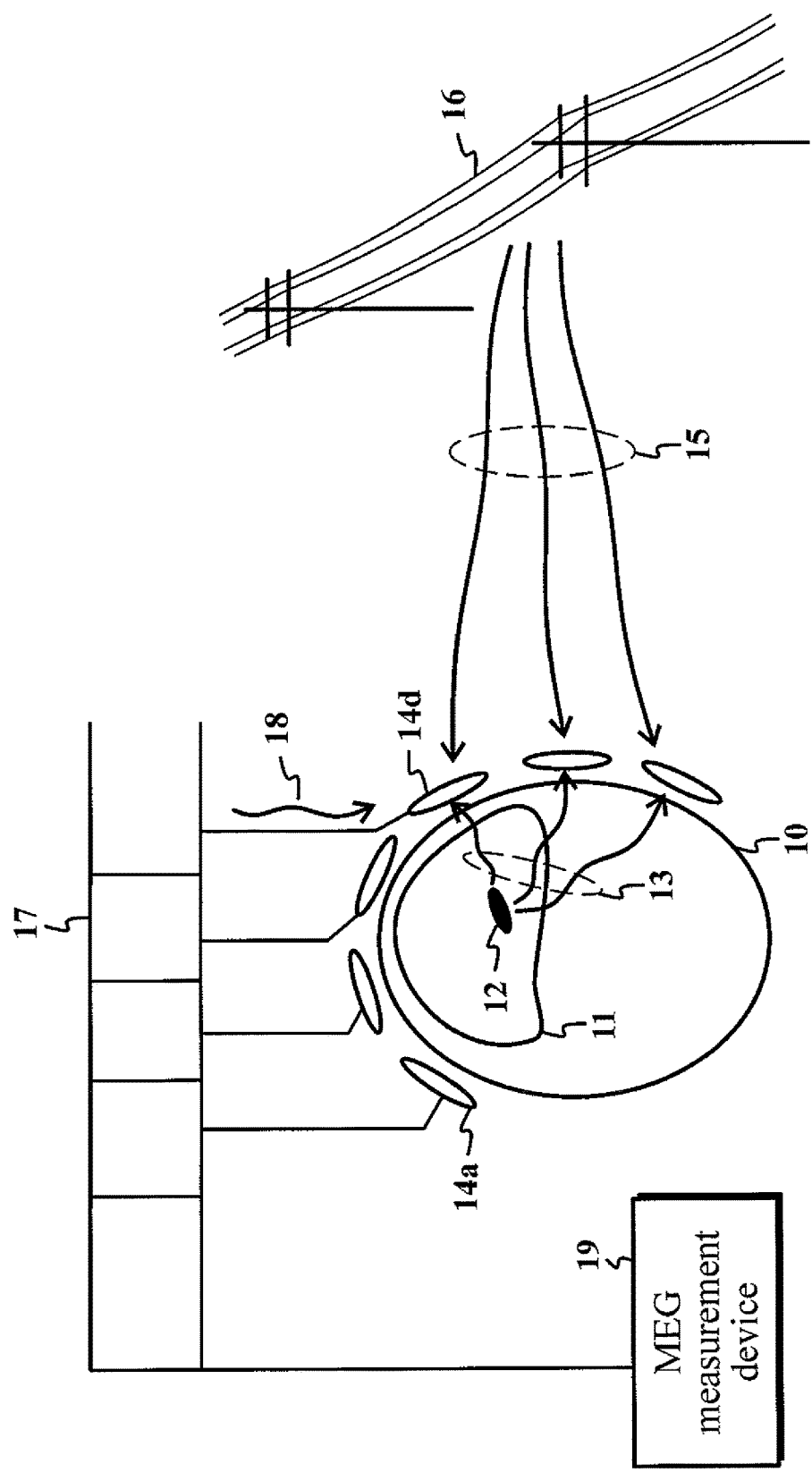

signal vector is decomposed into n+m components in the combined basis, and finally, components corresponding to the m added vectors in the combined basis are subtracted from the recorded N-dimensional signal vector.

23 Claims, 4 Drawing Sheets

(51) Int. Cl.
*A61B 5/04* (2006.01)
*G01R 33/035* (2006.01)
*G01R 29/12* (2006.01)
*G01R 33/02* (2006.01)
*G01R 33/56* (2006.01)
*G06K 9/00* (2006.01)
*A61B 5/0476* (2006.01)
*A61B 5/055* (2006.01)

(52) U.S. Cl.
CPC ........... *G01R 33/035* (2013.01); *G01R 33/56* (2013.01); *A61B 5/0024* (2013.01); *A61B 5/04008* (2013.01); *A61B 5/0476* (2013.01); *A61B 5/055* (2013.01); *G06K 9/0051* (2013.01)

(56) References Cited

FOREIGN PATENT DOCUMENTS

| WO | 2004081595 | 9/2004 |
|----|------------|--------|
| WO | 2005030051 | 4/2005 |
| WO | 2012004458 | 1/2012 |
| WO | 2013111072 | 8/2013 |

OTHER PUBLICATIONS

Japanese Patent Office Action for Application No. 2014-553840 dated Aug. 30, 2013 with English Translation (10 pages).
Taulu, S. et al., "Spatiotemporal Signal Space Separation method for rejecting nearby interference in MEG measurements," Phys. Med. Biol. 51 (2006) pp. 1759-1768.
Ozkurt, T. E et al., "Decomposition of Magnetoencephalographic Data Into Components Corresponding to Deep and Superficial Sources," IEEE Transactions on Biomedical Engineering, vol. 55, No. 6, Jun. 2008, pp. 1716-1727.
Vrba, J. et al., "Signal Space Separation Beamformer," Brain Topogr. (2010) 23:128-133.
Medvedovsky, M. et al., "Fine tuning the correlation limit of spatia-temporal signal space separation for magnetoencephalography," Journal of Neuroscience Methods, 177 (2009) pp. 203-211.
Taulu, S. et al., "Applications of the Signal Space Separation Method", IEEE Transactions on Signal Processing, vol. 53, No. 9, Sep. 2005, pp. 3359-3372.
Foster, M., "An Application of the Wiener-Kolmogorov Smoothing Theory to Matrix Inversion", Journal of the Society for Industrial and Applied Mathematics, vol. 9, No. 3, Sep. 1961.
Alain de Cheveigne et al., "Sensor noise suppression," Journal of Neuroscience Methods, 168, 30 (2008) pp. 195-202.
International Search Report for Application No. PCT/IB2013/050595 dated Jun. 25, 2013 (4 pages).

* cited by examiner

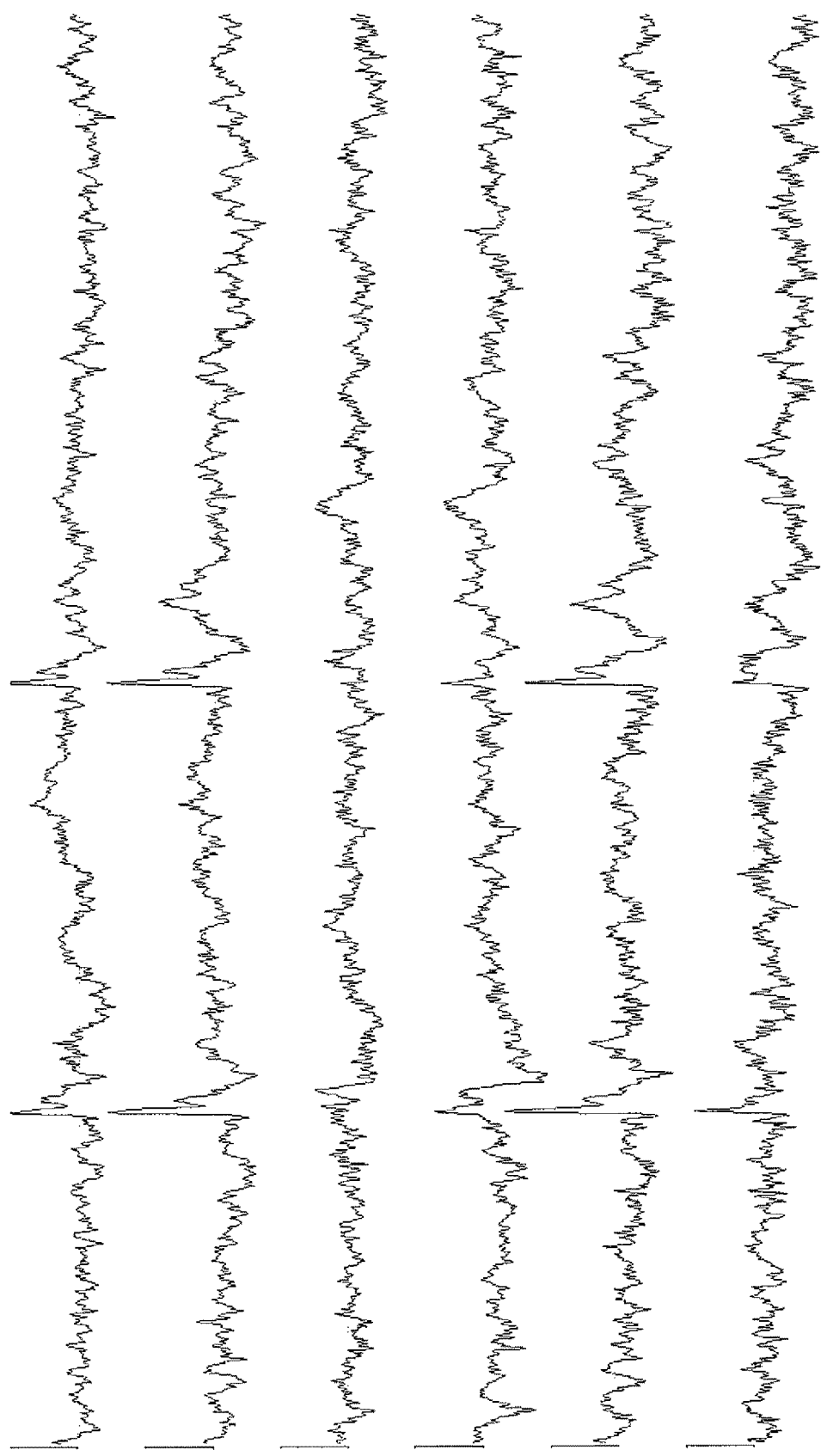

METHOD AND DEVICE FOR RECOGNIZING AND REMOVING UNDESIRED ARTIFACTS IN MULTICHANNEL MAGNETIC FIELD OR ELECTRIC POTENTIAL MEASUREMENTS

FIELD OF THE INVENTION

The invention relates to multichannel measurements applied e.g. in magnetoencephalography (MEG), electroencephalography (EEG) and magnetic resonance imaging (MRI), and especially to improving the quality of the results of such measurements.

BACKGROUND OF THE INVENTION

Particularly in medical research, various imaging methods are used in the analysis of tissue structures and brain signals. Modern physiological recording and imaging is made using sensor arrays comprising several tens or hundreds of sensors performing parallel recording of the neural activity. Such multi-channel devices are used for example in magnetoencephalography (MEG), where MEG means the measurement and analysis of magnetic fields generated by the electric activity of the brain. Electroencephalography (EEG) measures electric potentials in desired parts of the patient. A further multichannel measurement application is magnetic resonance imaging (MRI), simply referred as magnetic imaging. The MRI is applicable to different parts of the body and it uses multiple receiver coils.

It is typical of the imaging methods that a large set of measurement channels and related measurement sensors are needed therein. The signal recorded by each individual sensor in these multichannel devices contains both information on the neural activity (or on precession of nuclear magnetization in case of MRI), and interference from environmental sources, and artifacts and random noise related to the sensor technology. Since the neurological electric and magnetic fields are very weak, such sensor noise tends to hamper the detection of the interesting neurological signals. Therefore, the sensors must have very low-noise characteristics and they should be situated close to the measured object. The typical noise level of a measurement sensor measuring a magnetic field is of the order of a few femtoteslas. It is characteristic to the biomagnetic measurements that the magnetic flux densities to be measured are very low (for example of the order of 10 . . . 1000 fT), and the external interference fields prevailing in the measurement situation may be quite large in comparison to the flux densities, even of the order of 1 . . . 10 µT. The estimation of the portion of different interference signals in the overall measurement signal and the elimination of the effect of interferences from measurement results is thus extremely essential in multichannel biomagnetic measurement methods.

Additionally, artifacts (such as sudden spikes and jumps) related to individual channels may be misinterpreted to represent real neural activity, such as interictal epileptic spiking, for example. Therefore, from the point of view of clinical utilization of these multichannel technologies, both artifacts and random sensor noise should be removed or damped as much as possible.

A calculatory method used in the analysis of measured signals and to reject environmental interference from multichannel MEG signals is the so-called Signal Space Separation method (abbreviated as the SSS method), which is discussed for example in patent publication FI 115324. The SSS method is currently quite amply used in the art. It is a calculatory method for separating multichannel measurement signal information, on the basis of the locations of the sources, into various signal bases, i.e. subspaces that are linearly independent of one another. The SSS is purely based on the geometry of the sensor assembly and natural laws. The calculation according to the principle of the SSS begins by applying Maxwell's equations describing the relations of electric and magnetic fields. In the SSS method, it is possible to separate the magnetic fields generated by the useful sources (such as the brain) and the magnetic fields originating from external interference sources. In other words, series developments are calculated in the SSS method using division according to sources located in different sites. It may be referred to as a source modeling method for the multichannel measurement signal in a volume where the magnetic fields to be determined are irrotational and sourceless. The SSS method does not need advanced information about the types or locations of the different signal sources but it works correctly in the cases of different types of signal sources, also when examined as a function of time even when the location and/or intensity of the sources changes. In the calculation according to the SSS method, the geometry of the sensor assembly thus plays an important role. Associated to the geometry is also the fact that, in addition to the location, the orientation of the sensors significantly affects the measured signal because the magnetic field is a direction-dependent quantity.

Describing in other words the SSS method in general, an n-dimensional basis, the so-called SSS-basis, is formed for the N-dimensional signal space of the N-channel MEG device. The number of basis vectors n is smaller than N. The basis vectors are chosen so that each of them corresponds to a physically possible magnetic field shape in a source free space. Furthermore, based on the asymptotic behaviour of the corresponding magnetic potential functions, when $r \to 0$ and $r \to \infty$, these basis vectors are divided into two groups: the ones that correspond to magnetic fields arising from sources inside of the MEG sensor helmet, and the others corresponding to magnetic fields arising from sources in the environment, outside of the MEG helmet. The former group contains the field of interest, arising from neuromagnetic sources, and the latter group contains the environmental interference contribution to the signals that is wanted to be removed. The basic idea of the SSS method is to simply leave out from the SSS-basis representation of the recorded signals the components belonging to the latter group, and thus, the desired biomagnetic signal is achieved more accurately.

An advantage of the SSS method is that it can observe all interferences regardless of time and place. Since the calculation is made independently for each sample, it observes the changing situations regardless of whether the interference sources are changing inside or outside the measurement area, which can be e.g. a magnetically shielded room. A problem of the SSS method is that it is sensitive to calibration errors. This means that, for example, a signal deviation measured by one of the sensors may not be due to interference but a small unrecognized deviation in the position or direction (angle of its axis) of the sensor.

The main problem of the prior art is that, even by using solely the SSS method, any artifacts or peculiarities emerging in any of the sensors or measurement channels are left outside of the SSS-based signal modeling, and are therefore still hard to handle in the biomagnetic measurements and their calculatory analysis. In other words, in case a channel starts to behave in an odd manner, the noise level will rise and weaken the measurement results' quality significantly.

OBJECTIVE OF THE INVENTION

The objective of the invention is to disclose a method for getting rid of artifacts and noise present in individual sensors for multichannel measurements made using MEG, EEG or MRI imaging devices. A further objective of the invention is to remedy the above-mentioned problems.

SUMMARY OF THE INVENTION

The present invention introduces a method for recognizing and removing undesired artifacts in at least one measurement channel of a multichannel magnetic field or electric potential measurement, wherein a measurement device comprises a set of N measurement sensors and a data processing logic, and wherein the method comprises the step of generating a basis defining an n-dimensional subspace of the N-dimensional signal space, where n is smaller than N, using in the definition of the n-dimensional basis a physical model of a Signal Space Separation method, or a statistical model based on the statistics of recorded N-dimensional signals.

The method is further characterized in that the method further comprises the steps of forming a combined (n+m)-dimensional basis by adding m signal vectors to the n-dimensional basis, each of these m signal vectors representing a signal present only in a single channel of the N-channel device, decomposing the recorded N-dimensional signal vector into n+m components in the combined basis, and subtracting from the recorded N-dimensional signal vector the components corresponding to the m added vectors in the combined basis.

In an embodiment of the present invention, the signal is recorded at a spatial sampling rate exceeding the highest spatial frequencies in the signal of interest, so that n+m is smaller than N.

In an embodiment of the present invention, only one basis vector is added, representing the signal in this one channel only, to the n-dimensional basis, where m is equal to 1.

In an embodiment of the present invention, the decomposition of the recorded signal into the n+1 components in the combined basis is repeated N times, using as the one additive basis vector a vector corresponding to each one of the channels at a time, and the N signal components corresponding to the additive basis vectors are subtracted in each decomposition from the original data.

In an embodiment of the present invention, a solution of a linear problem related to the decomposition of the N-dimensional signal into the n+m components is numerically stabilized by using the Wiener-Kolmogorov method described by Foster (Manus Foster in "An Application of the Wiener-Kolmogorov Smoothing Theory to Matrix Inversion, J. Soc. Indust. Appl. Math., volume 9, no. 3, September 1961") or by any similar regularization method.

In an embodiment of the present invention, statistical correlations of the sensor noise between the N channels are estimated, which correlations are needed in the numerical regularization method, from differences between consecutive samples in the recorded signals.

In an embodiment of the present invention, the statistical correlations of the sensor noise between the N channels are estimated from the correlations in high-pass filtered recorded signals.

In an embodiment of the present invention, the signal is recorded at a temporal sampling rate exceeding the highest frequencies in the signal of interest.

In an embodiment of the present invention, the steps of forming, decomposing and subtracting are realized by a cross validation method where the signal of m channels are derived from the signals of the other N-m channels based on the n-dimensional physical model, or based on the n-dimensional statistical model of the original N-dimensional signal.

In an embodiment of the present invention, the method is applied to recordings made by a multi-channel magnetoencephalography (MEG) device.

In an embodiment of the present invention, the method is applied to recordings made by a multi-channel electroencephalography (EEG) device.

In an embodiment of the present invention, the method is applied to recordings of magnetic resonance signals obtained by a multichannel MRI device.

According to a second aspect of the present invention, the inventive idea comprises a multichannel measurement device arranged to recognize and remove undesired artifacts in at least one measurement channel of a multichannel magnetic field or electric potential measurement, wherein the measurement device comprises a set of N measurement sensors, and a data processing logic, which is arranged to generate a basis defining an n-dimensional subspace of the N-dimensional signal space, where n is smaller than N, using in the definition of the n-dimensional basis a physical model of a Signal Space Separation method, or a statistical model based on the statistics of recorded N-dimensional signals. The data processing logic is further characterized by that it is arranged to form a combined (n+m)-dimensional basis by adding m signal vectors to the n-dimensional basis, each of these m signal vectors representing a signal present only in a single channel of the N-channel device, decompose the recorded N-dimensional signal vector into n+m components in the combined basis, and subtract from the recorded N-dimensional signal vector the components corresponding to the m added vectors in the combined basis.

In an embodiment of the measurement device, the set of N measurement sensors is further arranged to record the signal at a spatial sampling rate exceeding the highest spatial frequencies in the signal of interest, so that n+m is smaller than N.

In an embodiment of the measurement device, the data processing logic is further arranged to add only one basis vector, representing the signal in this one channel only, to the n-dimensional basis, where m is equal to 1.

In an embodiment of the measurement device, the data processing logic is further arranged to repeat the decomposition of the recorded signal into the n+1 components in the combined basis N times, using as the one additive basis vector a vector corresponding to each one of the channels at a time, and subtract the N signal components corresponding to the additive basis vectors in each decomposition from the original data.

In an embodiment of the measurement device, the data processing logic is further arranged to stabilize numerically a solution of a linear problem related to the decomposition of the N-dimensional signal into the n+m components by using the Wiener-Kolmogorov method described by Foster or by any similar regularization method.

In an embodiment of the measurement device, the data processing logic is further arranged to estimate statistical correlations of the sensor noise between the N channels, which correlations are needed in the numerical regularization method, from differences between consecutive samples in the recorded signals.

In an embodiment of the measurement device, the data processing logic is further arranged to estimate the statistical correlations of the sensor noise between the N channels from the correlations in high-pass filtered recorded signals.

In an embodiment of the measurement device, the data processing logic is further arranged to record the signal at a temporal sampling rate exceeding the highest frequencies in the signal of interest.

In an embodiment of the measurement device, the data processing logic is further arranged to realize the steps of forming, decomposing and subtracting by a cross validation method where the signal of m channels are derived from the signals of the other N-m channels based on the n-dimensional physical model, or based on the n-dimensional statistical model of the original N-dimensional signal.

In an embodiment of the measurement device, the device is a multichannel magnetoencephalography (MEG) device.

In an embodiment of the measurement device, the device is a multichannel electroencephalography (EEG) device.

In an embodiment of the measurement device, the device is a multichannel magnetic resonance imaging (MRI) device obtaining magnetic resonance signals.

According to a third aspect of the present invention, the inventive idea further comprises a computer program for recognizing and removing undesired artifacts in at least one measurement channel of a multichannel magnetic field or electric potential measurement, wherein a measurement device comprises a set of N measurement sensors and a data processing logic. The computer program comprises program code which, when run on the data processing logic, is arranged to execute the step of generating a basis defining an n-dimensional subspace of the N-dimensional signal space, where n is smaller than N, using in the definition of the n-dimensional basis a physical model of a Signal Space Separation method, or a statistical model based on the statistics of recorded N-dimensional signals. The computer program is characterized by that it is further arranged to execute the steps of forming a combined (n+m)-dimensional basis by adding m signal vectors to the n-dimensional basis, each of these m signal vectors representing a signal present only in a single channel of the N-channel device, decomposing the recorded N-dimensional signal vector into n+m components in the combined basis, and subtracting from the recorded N-dimensional signal vector the components corresponding to the m added vectors in the combined basis.

In an embodiment of the computer program, the computer program is stored on a medium readable by the data processing logic.

LIST OF FIGURES

Figure 2:
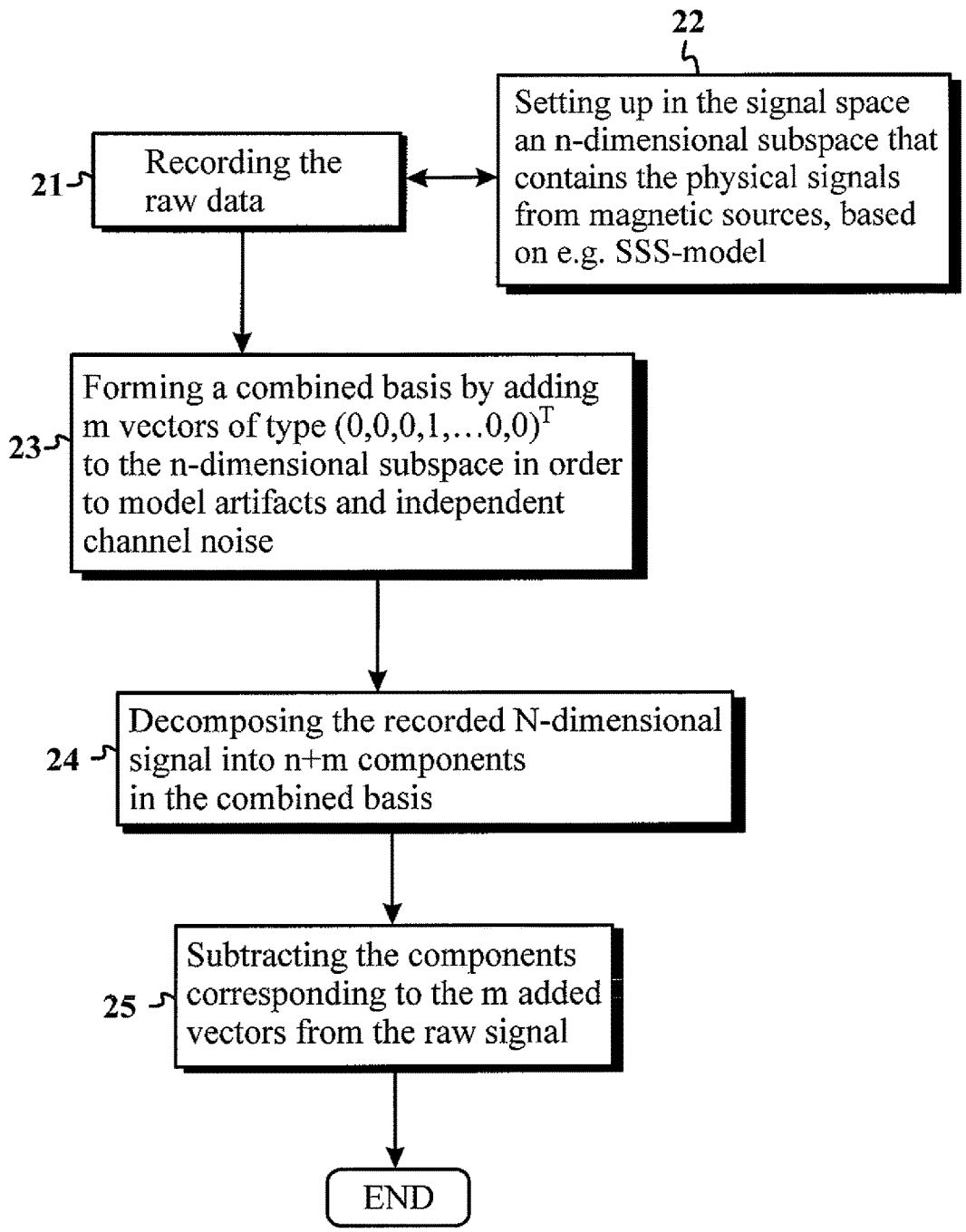
Figure 3A:
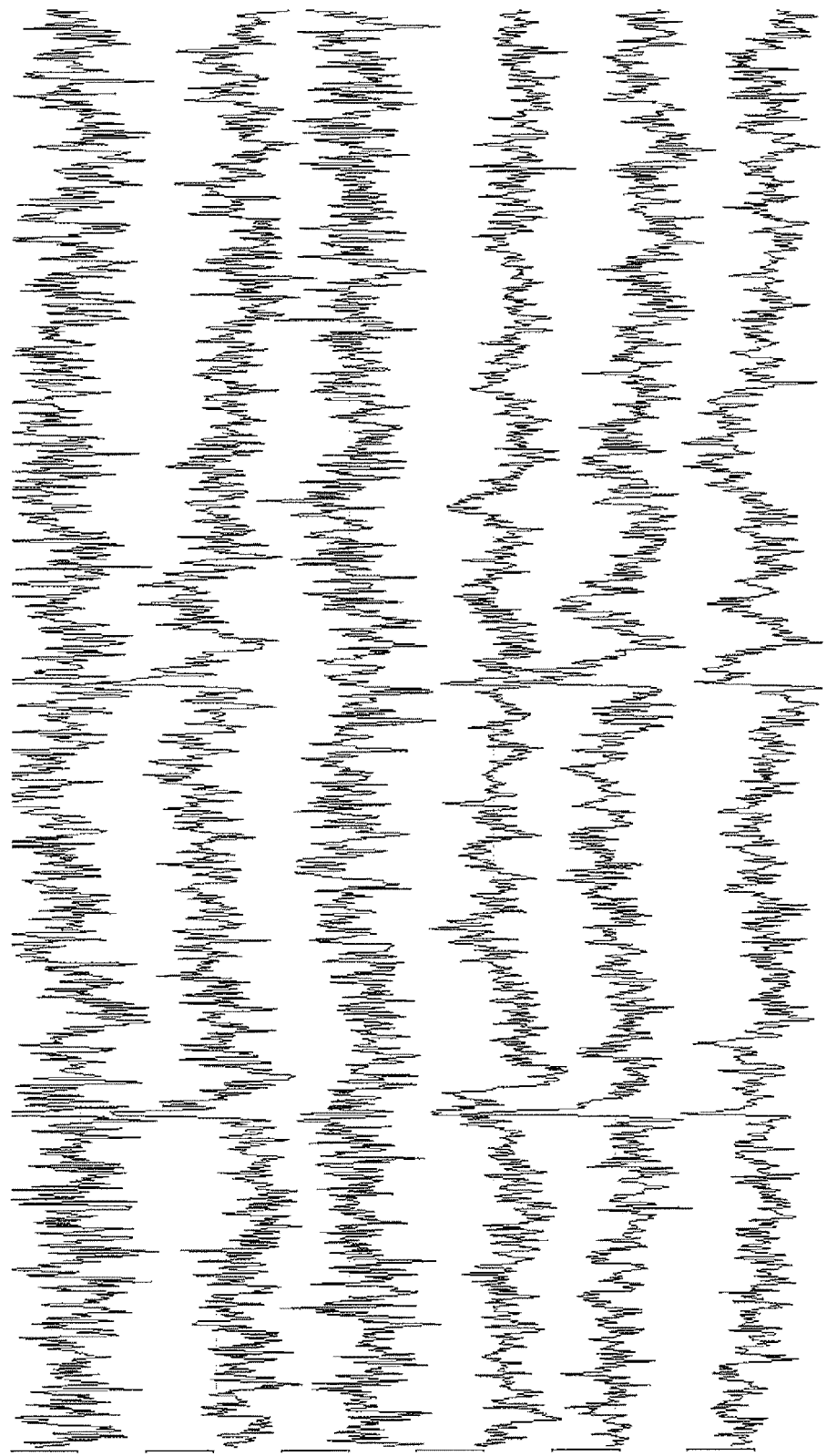

FIG. 1 shows an example of the measurement arrangement of an MEG apparatus, including different types of magnetic signals present in the system, FIG. 2 shows an example of the method according to the invention in the form of a flow chart, and FIGS. 3a and 3b graphically illustrate an example of the effect of the present invention.

DETAILED DESCRIPTION OF THE INVENTION

The present invention introduces a method for identifying and removing artifacts and sensor-specific interference signals in multichannel magnetic measurements.

The present invention is related to suppression of individual sensor noise and artifacts in a multichannel measurement containing N measurement channels. The basis of the algorithm described here is a comprehensive n-dimensional (n<N) signal model that describes the magnetic signal in magnetoencephalography (MEG) measurements. The aim is to build this model in such a way that any deviation from the model can only be explained as measurement errors of individual sensors, which are also uncorrelated with all other sensors. Such errors are typically caused by random sensor noise or electronics-based artifacts.

As an exemplary embodiment of the present invention, to detect and remove the channel noise and artifacts in an optimal manner, a method is proposed based on a physical model of the magnetic field in a source free volume, and applying an ample spatial and temporal oversampling provided by a modern MEG device having the number of measurement channels N=200 . . . 300, and the sampling frequency of several kHz.

The principle of the invention preferably is based on the Signal Space Separation method, abbreviated as the SSS method, which has been summarized above. In the SSS method, the central idea is that by utilizing Maxwell's equations and information about the geometry of the sensor assembly, it is possible to calculate a result indicating which part of the measured signal comprises of interesting biomagnetic signals originating from inside the measurement sensors and which part comprises the external interferences originating from outside the volume defined by the sensors. By such volume it is typically meant a sensor helmet which is placed around the patient's head, in case of brain signal measurements. In the SSS method, the magnetic multipole moments, i.e. the weights of signal components, in a linearly independent signal basis of the useful signal and, in turn, in a signal basis formed by interference signals, can be calculated. Being a real-time method, the SSS method adapts to currently prevailing interference situation, i.e. the SSS method always measures the real prevailing magnetic field, regardless of the changes of the signal sources inside or outside the volume to be measured that normally may occur as a function of time. The results provided by the SSS method are, however, affected by the above-mentioned calibration error, i.e. the inaccuracy in the sensitivity, location and positions of the measurement sensors (the supposed location and position information compared with the real location and position information) directly affects the results provided by the SSS method. To reduce the effect of this calibration inaccuracy, a method combining SSS with a signal modeling method based on the statistics of the recorded signal (principal component analysis, PCA) is described in application FI 20105769. Relating closely to this issue, any spikes, jumps or other kinds of behaviour not related to physical fields but rather on channel artifacts visible in one measuring channel only (or in several channels, independently) is the phenomenon on which the following really concentrates to.

In one embodiment of the present invention, an SSS basis for the measured multichannel signal is first defined, similarly as it has been done in the prior art. In addition to the external interferences, it is also desired to get rid of the artifacts and noise of the individual sensors. To achieve this, one more basis vector is added to the n-dimensional SSS-basis:

(0, 0, 0, . . . , 0, 1, 0, . . . , 0, 0).

This basis vector describes the part of the N-dimensional signal that is seen in the kth channel only, with no correlation to the signals of the other N−1 channels. Such an uncorrelated signal must be due to the artifacts and noise of the kth channel itself, when the sensor density (spatial oversampling from point of view of neuromagnetic sources) is high enough. In the method according to the present invention, the signal component falling on this new basis vector is left out from the signal. It may be the only component left out from the signal in case it is wanted to reject the sensor noise and occasional artifacts only, or it can be left out together with other outside originated interference components of the SSS-basis if the outside interference is also desired to be removed. To remove the sensor noise from all channels, this procedure is repeated for each of the N channels by including the corresponding additional vector to the SSS-basis. This is the part describing the "physical model" of the present invention. In this method, the channel noise is modeled in a similar way as the external interference is modeled in the SSS-method.

The method described here can be also considered as a kind of cross-validation method based on spatial oversampling, and on a rigorous model for the physical signal (magnetic field in a source free space).

The same physical model applies also to multichannel magnetic resonance imaging (MRI) recordings where the measured quantity is the magnetic field from the processing nuclear magnetization. Recently, low field MRI has been proposed to be realized using SQUIDs (Superconducting Quantum Interference Device) to gain good enough signal-to-noise ratio (SNR) even at magnetic fields in the range 20 µT-10 mT. To gain enough signal in such techniques, utilization of higher polarizing fields pulsed up and down during the measurement cycle have also been proposed (see PCT/US03/03712). SQUID-based sensors are known to be very sensitive to magnetic fields and rapid changes of the fields as well. Therefore, in any such MRI application, it will be practically unavoidable that sensor artifacts and elevated noise levels will show up in some of the sensors of a multichannel array after every polarization sequence. The method described in this invention helps to solve this problem related to low field MRI.

For EEG measurement applications, a simple physical model similar to that used in the magnetic applications does not exist. The relations between electric potentials recorded by EEG electrodes adjacent to each other are much more complicated and they depend on details of the head geometry and conductivity distributions. In this case, the "physical model" can be based on statistics, for example on a principal component analysis (PCA) of the multichannel EEG recordings. Such an approach has been described in "Alain de Cheveigne, Jonathan Z. Simon, Sensor noise suppression, Journal of Neuroscience Methods 168 (2008) 195-202" which discusses interpolation of the sensor signal from the neighbouring sensors. In de Cheveigne's publication, a set of statistically dominating features is extracted from the multichannel measurement and this set is then used as a model by which the aforementioned sensor-specific noise can be estimated in a cross-validated sense. Here cross-validation means that each channel is separately left out from the model and the data and then the signal of the channel under investigation is estimated by interpolating its signal from the neighbouring channels through the signal model. However, in order to achieve a reliable and generally applicable cross-validation based sensor noise and artifact suppression algorithm, one has to be able to construct a linearly independent n-dimensional general model for the signal of interest in such a way that n<N is always true. Statistical means alone do not guarantee applicability of such an approach.

Another possible application related to present invention may be high-$T_c$ MEG, i.e. high temperature superconductors in MEG. It is well known that changing from low-$T_c$ (e.g. niobium) SQUID technology to high-$T_c$ SQUID technology in MEG would greatly reduce the running costs if the MEG device could then implement simplified cryogenic technology. The basic factor preventing such development so far has been the considerably higher sensor noise in the high-$T_c$ SQUIDs ("J. Clarke, A. I. Braginski (eds.) The SQUID Handbook, Vol 1, Fundamentals and Technology of SQUIDs and SQUID Systems, Wiley VHC, 2004"). The method of the present invention will reduce this sensor noise by roughly a factor of square root of N. This enables construction of a useful high-$T_c$ based MEG system if N=200 . . . 300.

The n-dimensional signal basis described above for MEG and MRI applications is not an orthogonal basis in the N-dimensional signal space. Therefore, the linear operation needed to convert the recorded N-dimensional signal vector into the n-dimensional physical representation becomes increasingly unstable numerically, when n approaches N. This tends to increase noise in the n-dimensional representation of the physical signal and thus counteracts the intended noise reduction. To reduce this effect, the ratio n/N must be kept as low as possible. This means that ample spatial oversampling of the neuromagnetic field is necessary for successful application of the method described here. The number of channels, N, must clearly exceed the number of magnetic degrees of freedom (field shapes) that are included in the physical model. This number of degrees of freedom in MEG geometry has been shown to be about 15+80 (external interference+neuromagnetic field shapes), see "Taulu S., Simola J. and Kajola M.: Applications of the Signal Space Separation Method. IEEE Trans. Sign. Proc. 53 (2005) 3359-3372".

In addition to spatial oversampling, the adverse effect of the numerical instability of the required matrix inversion (pseudoinversion because n<N) can be controlled by doing the inverse operation in an optimally smooth manner. One method to achieve this is described by Manus Foster in "An Application of the Wiener-Kolmogorov Smoothing Theory to Matrix Inversion, J. Soc. Indust. Appl. Math., volume 9, no. 3, September 1961". Foster utilizes the sensor covariance estimate in a linear model, and it is an elegant regularization algorithm for matrix inversion which requires a good estimate for the sensor noise covariance. This covariance estimate describes the sensor noise and artifacts in a statistical manner and its main purpose is to stabilize the matrix inversion used in decomposing the measured multichannel signals into the basis components of the signal model.

In any realization of a multichannel MEG device, with all the sensors in immediate vicinity of each other (meaning "ample spatial oversampling") and provided with modern and compact electronics, there are numerous mechanisms that enable complicated and unpredictable noise correlation. The best way to reliably estimate noise correlation within an MEG device is to determine this correlation from the data itself. This means that the signals must be recorded over a frequency band wide enough to enable separation of the noise correlation from the correlation that exists in the neuromagnetic or environmental magnetic signal. Therefore, in addition to spatial oversampling, also ample temporal oversampling, by far exceeding the interesting signal band (0-600 Hz), is needed to enable reliable separation of sensor noise from neuromagnetic signal, and estimation of noise correlation, which then allows an optimally smooth pseudoinversion on the [(n+1)×N] matrix. Without such optimization, the advantage gained by removing the independent sensor noise could be partly or completely masked by the increase in noise due to numerical instability of the matrix inversion operation.

In order to describe the present invention in a more precise manner, a mathematical approach is next discussed. This mathematical approach is technically linked to the multichannel measurements of the MEG, EEG and MRI applications, and it is thus only an analysis tool for suppressing artifacts and noise from the individual measurement channels. As said already above, the present invention is based on utilization of spatial oversampling of the detectable features in a multichannel measurement and further enhanced by utilization of temporal oversampling for accurate estimation of random noise covariance patterns. Spatial oversampling means here that the number of measurement channels substantially exceeds the number of degrees of freedom, where the degrees of freedom represent different field shapes included in the physical model of the measurement arrangement. Temporal oversampling means here that signals are measured on a substantially wider frequency band than the frequency band of the useful signal.

More specifically, the mathematical algorithm can be described as follows. Let us first denote the general multichannel model as $$m = Ax + n \tag{1}$$

where m is the N-dimensional instantaneous measurement signal with each element corresponding to one individual channel, A is the [N×n]-dimensional signal model, x is the n-dimensional amplitude or coordinate vector corresponding to the components of A, and n corresponds to the measurement noise, i.e., any signal not related to model A. First of all, A will be developed in such a way that it always covers all degrees of freedom in the actual detectable signal of interest, so that only sensor noise and measurement artifacts fall into n. To meet this goal, A should be physically general and as insensitive to calibration errors as possible. It is previously shown in the case of MEG application that such a physical model exists and it can be furthermore divided geometrically into the internal, containing the human brain, and external, only containing interference fields, parts as:

$$A = [S_{in} S_{out}] \tag{2}$$

This model is called as the signal space separation (SSS) model and it has been shown to be linearly independent for any practical multichannel sensor array. To further improve the insensitivity to calibration errors, so-called empty room signals without any subject may be measured, perform a statistical analysis, typically the principal component analysis (PCA), and add any deviation of the dominating PCA components into the computational interference part as $$S'_{out} = [S_{out} \delta] \tag{3}$$

where δ stands for such a deviation (see patent application FI 20105769). In the present invention, the model is further modified to include individual sensor noise and artifacts. It is assumed that the model A spans all signals of interest and a model for the individual signal of the j:th channel is added in the following way:

$$A_j = [A u_j] \tag{4}$$

where $u_j$ is a unit vector having its only non-zero element on channel j. Thus, corresponds to a signal that is only seen on channel j and that cannot be estimated from the signal of any other channel. Now, eq. (1) transforms into $$m = A_j x_j + n_j \tag{5}$$

where $x_j = [x; n_j]$ and $n_j$ is otherwise as n but the j:th element of $n_j$ is zero. By solving for $x_j$ in eq. (5), an estimate can be achieved for the individual signal of the j:th channel as the time-dependent variable $n_j(t)$, which is the last element of vector $x_j$ according to eq. (5). It is straightforward to show that this operation is mathematically equivalent to an algorithm resembling cross-validation, where one can solve for x from eq. (1) by leaving out the j:th channel from m and A and then calculate the estimate $n_j(t)$ by $$n_j(t) = m_j(t) - a_j \cdot x'_j(t) \tag{6}$$

where $x'_j(t)$ stands for the estimate of x(t) without the contribution of the j:th channel and $a_j$ is the j:th column of the model A. In this way, the individual artifactual activity of the j:th channel will show up as the deviation given by the time-dependent variable $n_j(t)$.

The accuracy and reliability of sensor noise suppression is determined by the completeness and generality of the model A as well as the stability of matrix inversion needed to solve equations (1) or (5). It is shown before that in MEG, and probably in many other multichannel modalities, such a comprehensive model can be found. Furthermore, it is shown here that the cross-validation approach is equivalent to using orthogonal unit vectors $u_j$, which enables us to model the individual sensor activity for each sensor one by one by using eqs. (1) or (5) without any overlapping between the contributions of the sensor models ($u_j \cdot u_k = 0$ for j≠k). Finally, it is noted that if we also have temporal oversampling of the signal, i.e., our sampling frequency is much higher than the signal of interest to be modelled by, we can calculate a reliable estimate for the noise covariance matrix from the high end of the frequency contents of the signal so that we do not accidentally include the signal of interest in the covariance estimate. The covariance can be readily used in Foster's optimal inverse operation for a more accurate solution of eq. (1) or (5). The covariance estimate can be calculated even with the signal of interest present in the measurement, provided that we have temporal oversampling, because it can be mathematically proven that a covariance calculated from difference vectors between subsequent samples leads to a noise covariance corresponding to the true white noise covariance multiplied by a factor of two. Here temporal oversampling means that the difference vectors do not contain the signal of interest as it cancels out in the subtraction of two temporally close samples.

In order to describe the physical arrangement and situation in real-life magnetic field measurements, FIG. 1 is now referred and discussed. The object to be measured is a human head 10 in which the brain 11 produces signals which are interesting. An interesting source 12 produces interesting magnetic fields 13 originating in the brain 11. The MEG measurement device and especially the control electronics is shown in a simplified form as 17. The measurement channels represented by a plurality of measurement sensors 14a-f (only the first and fourth ones are marked in the figure for simplicity, and of course the total number of six sensors is only a simplified case of the actual measurement arrangement comprising usually several hundreds of sensors) are located e.g. as a helmet formation around the patient's head 10. All measurement sensors 14a-f are connected to the control electronics 17. The control logic of the system comprising a processor, memory and all other analysis tools are comprised in the MEG measurement device 19, connected to the control electronics 17 and the measurement sensors 14a-f.

The raw signal collected by a sensor 14d of the MEG device is a superposition of three contributions or signal types: The first one is formed by the interesting neuromagnetic signals represented by 13. The second one is generally all noise and interference from the environment, shown in the figure by large-capacity line 16, creating magnetic interfering field 15. The third kind of signal is relevant to the present invention; these are formed by the artifacts 18 related to an individual sensor 14d and its electronics 17. The SSS method is capable to separate the fields 13 of the interesting magnetic sources, and the fields 15 of the interfering magnetic sources 16. The present invention is further capable to separate the artifact 18 relating to the sensor 14d, and remove it from the magnetic field signal measured by sensor 14d. This is performed by the algorithm disclosed above in detail, run by the processor in the MEG measurement device 19. The results with much better S/N ratio can be seen in FIG. 3.

FIG. 2 illustrates a flow chart of the method according to an example of the invention. At first, the measurement arrangement is set up, by putting a measurement helmet comprising sensors around the patient's head, for example. In one example, the arrangement comprises 306 measurement sensors. The raw signal is recorded 21. At first, an n-dimensional "magnetic subspace" following SSS analysis according to prior art is set up 22. The SSS method separates the interesting magnetic sources from the interfering magnetic sources, the first ones locating inside the measurement helmet, and the others clearly outside the measurement helmet, usually outside the measurement room, too. The number of magnetic field shapes representing the interesting signals is in one example 80, and the number of magnetic field shapes representing the interferences signals is 15, for instance. Therefore, the subspace 22 is in this example a 95*306 matrix representing all signals originating from magnetic sources.

After this step, the artifact analysis of the invention is started by forming a combined basis by adding m vectors of type $(0,0,0, \ldots, 1,0,0, \ldots, 0)^T$ to the n-dimensional subspace in order to model artifacts and independent channel noise 23. The combination is made according to equation 4. In this example, the size of this vector is 306*1, and in case FIG. 2 would be concerned, element "1" would be the fourth element of the vector (k=4 in that case). In the following step 24, the recorded N-dimensional signal is decomposed into n+m components in the combined basis. Finally, the components corresponding to the m added vectors are subtracted from the raw signal 25.

FIGS. 3a and 3b illustrate two seconds of data from an MEG recording of human somatosensory response. Signals from six MEG channels are shown. The y-scale of the figures is illustrated by a vertical segment of a line whose length in this case is 200 fT/cm. In FIG. 3a, there is the original recorded raw data. In FIG. 3b, the same signals after processing the data with the method of the present invention are illustrated. The two somatosensory responses, simultaneously seen in five of the six channels, are clearly seen in the processed data. Only the sensor noise intrinsic to each channel has been removed in this case. The reduction in random sensor noise is about a factor of five. Most of the variation of the signals outside of the somatosensory response periods is from ongoing spontaneous brain activity independent from the somatosensory stimulus.

The present invention can even be applied in analyzing Gallup results of different kinds of polls where gathered results represent the opinions otherwise realistically, but there are some peculiar results which can be clearly regarded as not real opinions. Such opinions can be regarded as artifacts which need to be cleared from the results in order to achieve much more reliable poll result.

With using the present invention, sensors with higher noise characteristics may be used. Furthermore, superconductors applied in higher temperatures may be used in the used sensor technology. This relieves the requirements of cooling of the sensors, because higher temperatures are possible. The present invention is thus capable to reduce artifactual noise from the sensors by applying the presented method for all channels, one channel at a time by going through the algorithm with for all values k=1, . . . , N regarding the unit vector combining procedure.

Thus, the most important advantage of the present invention is that the artifactual noise in the set of measurement channels can be clearly reduced, improving the overall quality in analyzing the biomagnetic signals. Furthermore, the presented method is broadly applicable in many different applications, comprising multichannel magnetoencephalography, electroencephalography and magnetic resonance imaging measurements.

Furthermore, as practical application targets, patients with concussion of the brain or epilepsy will have efficient results when the multichannel measurements are applied to them and the algorithm of the present invention is therewith applied.

The steps of the method presented for the invention can be carried out in applicable parts as a computer program that can be run on the data processing logic of the MEG device, the EEG device or the MRI device i.e. typically on the processor of the device. The device may include a memory or other storage medium wherein the computer program, the data input and other parameters required by the method and the results obtained from the measurements can be stored.

The invention is not limited merely to the exemplifying embodiments referred to above; instead, many variations are possible within the scope of the inventive idea defined by the claims.

The invention claimed is:

1. A method for recognizing and removing undesired artifacts and sensor-specific interference signals in at least one measurement channel of a multichannel magnetic field or electric potential measurement, wherein a measurement device comprises a set of N measurement sensors and a data processing logic, and wherein the method comprises the step of:
   receiving, at an electronic processor, an N-dimensional signal from the set of N measurement sensors;
   recording the N-dimensional signal;
   generating, via the electronic processor, a basis defining an n-dimensional subspace of the N-dimensional signal space, wherein n is smaller than N, using, in the definition of the n-dimensional basis, a physical model of a Signal Space Separation method, or a statistical model based on the statistics of the recorded N-dimensional signal;
   characterized in that the method further comprises the steps of:
   forming a combined (n+m)-dimensional basis by adding m signal vectors to the n-dimensional basis, each of these m signal vectors representing a signal present only in a single channel of the N-channel device,
   decomposing the recorded N-dimensional signal into n+m components in the combined basis, and
   subtracting, from the recorded N-dimensional signal, the components corresponding to the m added vectors in the combined basis;

producing a modified N-dimensional signal by removing the undesired artifacts and sensor-specific interference signals, via the electronic processor, based on the recorded N-dimensional signal; and outputting, via the electronic processor, the modified N-dimensional signal;

wherein the N-dimensional signal is recorded at a temporal sampling rate exceeding the highest frequencies in a signal of interest and at a spatial sampling rate exceeding the highest spatial frequencies in a signal of interest, so that n+m is smaller than N.

2. The method according to claim 1, characterized by, adding only one signal vector, representing the N-dimensional signal in this one channel only, to the n-dimensional basis, where m is equal to 1.

3. The method according to claim 1, further characterized by, repeating the decomposition of the recorded N-dimensional signal into the n+1 components in the combined basis N times, using as the one additive basis vector a vector corresponding to each one of the channels at a time, and subtracting the N signal components corresponding to the additive basis vectors in each decomposition from the original data.

4. The method according to claim 1, further characterized by, stabilizing numerically a solution of a linear problem related to the decomposition of the N−15 dimensional signal into the n+m components by using a regularization method.

5. The method according to claim 4, further characterized by, estimating statistical correlations of the sensor noise between the N channels from differences between consecutive samples in the recorded signals.

6. The method according to claim 5, further characterized by, estimating the statistical correlations of the sensor noise between the N channels from the correlations in high-pass filtered recorded signals.

7. The method according to claim 1, characterized by the steps of forming, decomposing and subtracting are realized by a cross validation method where the signal of m channels are derived from the signals of the other N-m channels based on the n-dimensional physical model, or based on the n-dimensional statistical model of the original N-dimensional signal.

8. The method according to claim 1, further characterized by, applying the method to recordings made by a multichannel magnetoencephalography (MEG) device.

9. The method according to claim 1, further characterized by, applying the method to recordings made by a multichannel electroencephalography (EEG) device.

10. The method according to claim 1, further characterized by, applying the method to recordings of magnetic resonance signals obtained by a multichannel MRI device.

11. A multichannel measurement device arranged to recognize and remove undesired artifacts and sensor-specific interference signals in at least one measurement channel of a multichannel magnetic field or electric potential measurement, wherein the measurement device comprises a set of N measurement sensors arranged to record the N-dimensional signal at a spatial sampling rate exceeding the highest spatial frequencies in a signal of interest, so that n+m is smaller than N; and a data processing logic, which is arranged to receive and record, at an electronic processor, the N-dimensional signal from the set of N measurement sensors and record the signal at a temporal sampling rate exceeding the highest frequencies in a signal of interest and generate a basis defining an n-dimensional subspace of the N-dimensional signal space, wherein n is smaller than N, using, in the definition of the n-dimensional basis, a physical model of a Signal Space Separation method, or a statistical model based on the statistics of a recorded N-dimensional signal;

characterized in that the data processing logic is further arranged to:

form a combined (n+m)-dimensional basis by adding m signal vectors to the n-dimensional basis, each of these m signal vectors representing a signal present only in a single channel of the N-channel device, decompose the recorded N-dimensional signal into n+m components in the combined basis, and subtract, from the recorded N-dimensional signal, the components corresponding to the m added vectors in the combined basis;

produce a modified N-dimensional signal by removing undesired artifacts and sensor-specific interference signals, via the electronic processor, based on the recorded N-dimensional signal; and output, via the electronic processor, the modified N-dimensional signal.

12. The device according to claim 11, characterized in that the set of N measurement sensors is further arranged to:

record the N-dimensional signal at a spatial sampling rate exceeding the highest spatial frequencies in a signal of interest, so that n+m is smaller than N.

13. The device according to claim 11, characterized in that the data processing logic is further arranged to:

add only one signal vector, representing the signal in this one channel only, to the n-dimensional basis, where m is equal to 1.

14. The device according to claim 11, characterized in that the data processing logic is further arranged to:

repeat the decomposition of the N-dimensional recorded signal into the n+1 components in the combined basis N times, using as the one additive basis vector a vector corresponding to each one of the channels at a time, and subtract the N signal components corresponding to the additive basis vectors in each decomposition from the original data.

15. The device according to claim 11, characterized in that the data processing logic is further arranged to:

stabilize numerically a solution of a linear problem related to the decomposition of the N-dimensional signal into the n+m components by using a regularization method.

16. The device according to claim 15, characterized in that the data processing logic is further arranged to:

estimate statistical correlations of the sensor noise between the N channels from differences between consecutive samples in the recorded signals.

17. The device according to claim 16, characterized in that the data processing logic is further arranged to:

estimate the statistical correlations of the sensor noise between the N channels from the correlations in high-pass filtered recorded signals.

18. The device according to claim 11, characterized in that the data processing logic is further arranged to:

realize the steps of forming, decomposing and subtracting by a cross validation method where the signal of m channels are derived from the signals of the other N-m channels based on the n-dimensional physical model, or based on the n-dimensional statistical model of the original N-dimensional signal.

19. The device according to claim 11, characterized in that the device is a multichannel magnetoencephalography (MEG) device.

20. The device according to claim 11, characterized in that the device is a multichannel electroencephalography (EEG) device.

21. The device according to claim 11, characterized in that the device is a multichannel magnetic resonance imaging (MRI) device obtaining magnetic resonance signals.

22. A computer program for recognizing and removing undesired artifacts and sensor-specific interference signals in at least one measurement channel of a multichannel magnetic field or electric potential measurement, wherein a measurement device comprises a set of N measurement sensors and a data processing logic, and wherein the computer program comprises program code which, when run on an electronic processor, is arranged to execute the steps of:

receiving, at the electronic processor, an N-dimensional signal from the set of N measurement sensors;

recording the N-dimensional signal;

generating, via the electronic processor, a basis defining an n-dimensional subspace of the N-dimensional signal space, wherein n is smaller than N, using, in the definition of the n-dimensional basis, a physical model of a Signal Space Separation method, or a statistical model based on the statistics of a recorded N-dimensional signal;

characterized in that the computer program is further arranged to execute the steps of:

forming a combined (n+m)-dimensional basis by adding m signal vectors to the n-dimensional basis, each of these m signal vectors representing a signal present only in a single channel of the N-channel device, decomposing the recorded N-dimensional signal into n+m components in the combined basis, and subtracting, from the recorded N-dimensional signal, the components corresponding to the m added vectors in the combined basis;

producing a modified N-dimensional signal by removing the undesired artifacts and sensor-specific interference signals, via the electronic processor, based on the recorded N-dimensional signal; and outputting, via the electronic processor, the modified N-dimensional signal;

wherein the N-dimensional signal is recorded at a temporal sampling rate exceeding the highest frequencies in a signal of interest and at a spatial sampling rate exceeding the highest spatial frequencies in a signal of interest, so that n+m is smaller than N.

23. The computer program according to claim 22, characterized in that the computer program is stored on a medium readable by the electronic processor.

* * * * *